US009724317B2

(12) United States Patent
Lasser et al.

(10) Patent No.: US 9,724,317 B2
(45) Date of Patent: Aug. 8, 2017

(54) COMPOSITIONS AND METHODS FOR THE TREATMENT OF A COMMON COLD AND SYMPTOMS THEREOF

(71) Applicant: 3E THERAPEUTICS CORPORATION, La Jolla, CA (US)

(72) Inventors: Elliott C. Lasser, La Jolla, CA (US); Kenneth H. Lasser, La Mesa, CA (US)

(73) Assignee: 3E Therapeutics Corporation, La Jolla, CA (US)

( * ) Notice: Subject to any disclaimer, the term of this patent is extended or adjusted under 35 U.S.C. 154(b) by 0 days.

(21) Appl. No.: 15/004,775

(22) Filed: Jan. 22, 2016

(65) Prior Publication Data

US 2016/0136118 A1  May 19, 2016

Related U.S. Application Data

(63) Continuation of application No. 13/865,955, filed on Apr. 18, 2013, now Pat. No. 9,241,919, which is a continuation of application No. 12/903,120, filed on Oct. 12, 2010, now abandoned, which is a continuation of application No. 12/111,166, filed on Apr. 28, 2008, now abandoned.

(60) Provisional application No. 60/981,093, filed on Oct. 18, 2007, provisional application No. 60/914,642, filed on Apr. 27, 2007.

(51) Int. Cl.
  *A61K 31/194* (2006.01)
  *A61K 31/167* (2006.01)
  *A61K 9/00* (2006.01)
  *A61K 31/196* (2006.01)

(52) U.S. Cl.
  CPC ............ *A61K 31/194* (2013.01); *A61K 9/006* (2013.01); *A61K 9/0073* (2013.01); *A61K 31/167* (2013.01); *A61K 31/196* (2013.01)

(58) Field of Classification Search
  CPC .... A61K 31/167; A61K 31/196; A61K 9/006; A61K 9/0073
  See application file for complete search history.

(56) References Cited

U.S. PATENT DOCUMENTS

| 6,196,219 B1 | 3/2001 | Hess et al. |
| 6,427,682 B1 | 8/2002 | Klimowicz et al. |
| 2001/0002396 A1 | 5/2001 | Achkar |
| 2004/0198834 A1* | 10/2004 | Lasser .................. A61K 9/0043 514/616 |

FOREIGN PATENT DOCUMENTS

| EP | 0 363 829 | 4/1990 |
| WO | WO 03/035030 | 5/2003 |

OTHER PUBLICATIONS

Skoner (J Allergy Clin Immunol, vol. 108 (1), 2001, pp. S2-S8).*
(Continued)

*Primary Examiner* — Savitha Rao
(74) *Attorney, Agent, or Firm* — Pillsbury Winthrop Shaw Pittman, LLP

(57) ABSTRACT

Embodiments of the invention relate to methods and compositions for treating symptoms related to inflammatory conditions and to methods and compositions for treating inflammatory components of a common cold, utilizing various methods of administration od X-ray contrast media (CM).

15 Claims, 1 Drawing Sheet

(56) References Cited

OTHER PUBLICATIONS

De Sutter (Reprint of Cochrane review, published in The Cochrane Library, 2003 Issue 3).*
Hosoda et al. (J. Immunol, 2002, 169, pp. 1482-1491).*
Roitt et al.; Immunology, 1985, pp. 19.1, 19.7-19.10, Gower Medical Publishing Ltd., London, England.
Sampson; "Pathogenesis of Eczema", Clinical and Experimental Allergy, 1990, vol. 20, pp. 459-467.
Carr et al.; "Contrast media reactions: experimental evidence against the allergy theory", The British Institute of Radiology, vol. 57, Jun. 1984, pp. 469-473.
ContrastMedia_Schering document, 2005, retrieved from the internet on May 27, 2010, URL: http://web.archive.org/web/20050520234507/http:1/hsc.uwe.ac.uk/idis2/contrast_agents/CM+Zip/ContrastMedia_Schering.pdf.
Leung; "Molecular Basis of Allergic Diseases", Molecular Genetics and Metabolism, Mar. 1998, vol. 63, pp. 157-167.
Robert; Merck Manual, 2006, retrieved from internet on Jun. 4, 2010, URL:http://www.merck.com/mmhe/sec18/ch202/ch202c.htm.
Peachell et al.; "Effect of radiographic contrast media on histamine release from human mast cells and basophils" The British Journal of Radiology, Jan. 1998, vol. 71, pp. 24-30.
Demick; 2002, retrieved from internet on May 28, 2010, URL: http://www.essortment.com/all/typesrashesski_rnnu.htm.
Suto et al.; "Mast Cell-Associated TNF Promotes Dendritic Cell Migration", The Journal of Immunology, Apr. 1, 2006, vol. 176, pp. 4102-4112.
Emollient document by MedicineNet.com, retrieved from internet on May 28, 2010, URL: http://www.medicinenet.com/emollients-topical/article.htm, pp. 1-2.
Mazur et al.; "Increased angiogenesis in cutaneous T-cell lymphomas", Pathology & Oncology Research, Mar. 18, 2004, vol. 10, pp. 34-36.
Kawaguchi et al.; "Overexpression of tumor necrosis factor-alpha-converting enzyme in psoriasis", British Journal of Dermatology, May 2005, vol. 152, pp. 915-919.
Falanga et al.; "Elevated plasma histamine levels in systemic sclerosis (Scleroderma)", Archives of Dermatology, Mar. 1990, vol. 126, pp. 336-338.
Blaug; "Remington's Pharmaceutical Sciences" Mack publishing company, Easton PA, 15$^{th}$ edition, 1975, Ch. 87.
Fingl et al.; "The Pharmacological Basis of Therapeutics", Ch. 1, p. 1, 1975.

* cited by examiner

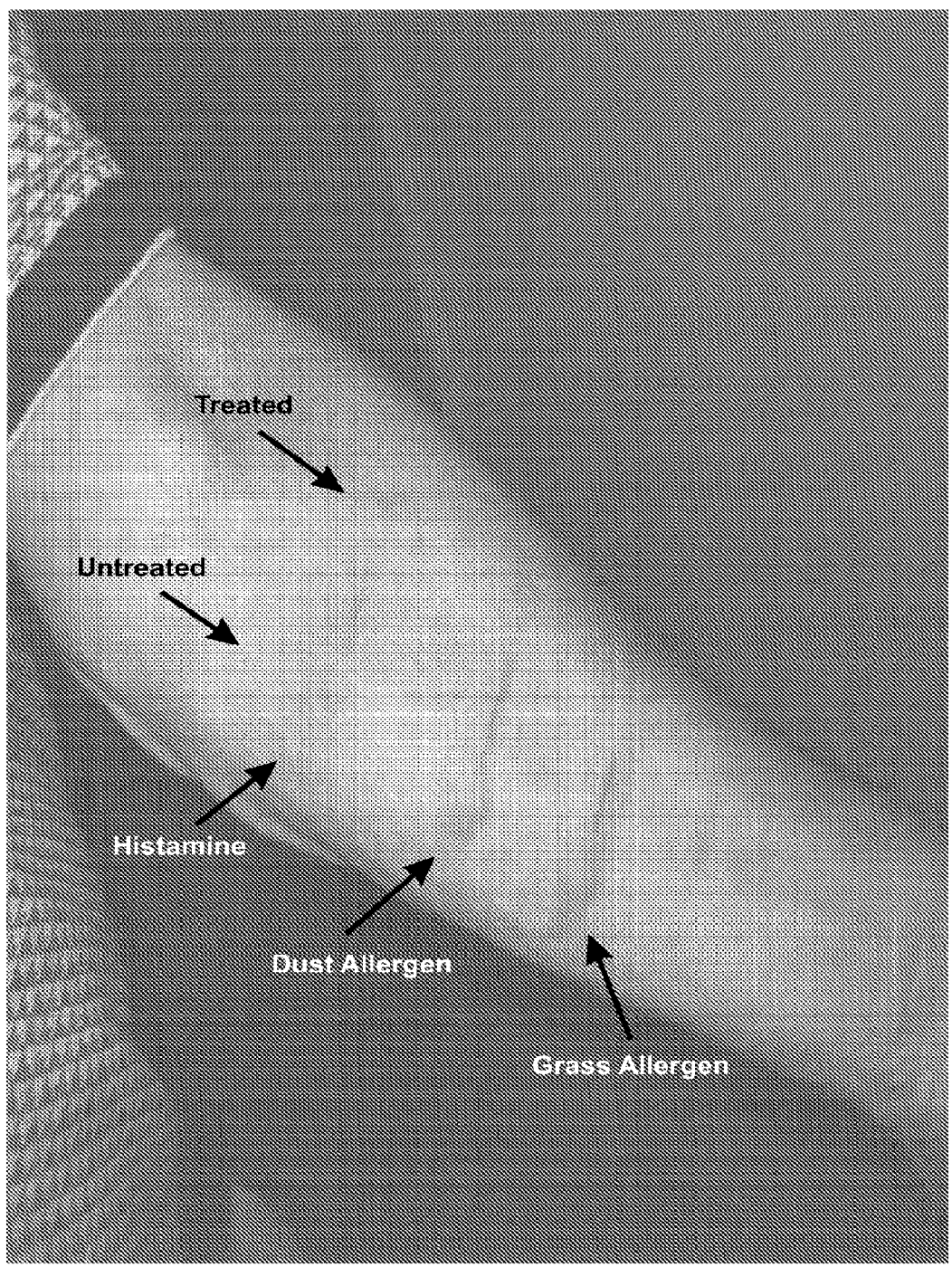

COMPOSITIONS AND METHODS FOR THE TREATMENT OF A COMMON COLD AND SYMPTOMS THEREOF

RELATED PATENT APPLICATIONS

This patent application is a continuation of, and claims the benefit of, U.S. patent application Ser. No. 13/865,955 filed on Apr. 18, 2013, entitled COMPOSITIONS AND METHODS FOR THE TREATMENT OF INFLAMMATORY CONDITIONS, naming Elliott C. Lasser and Kenneth H. Lasser as inventors; which is a continuation of, and claims the benefit of, U.S. patent application Ser. No. 12/903,120 filed on Oct. 12, 2010, entitled COMPOSITIONS AND METHODS FOR THE TREATMENT OF INFLAMMATORY CONDITIONS, naming Elliott C. Lasser and Kenneth H. Lasser as inventors, now abandoned; which is a continuation of, and claims the benefit of, U.S. patent application Ser. No. 12/111,166 filed on Apr. 28, 2008, entitled COMPOSITIONS AND METHODS FOR THE TREATMENT OF INFLAMMATORY CONDITIONS, naming Elliott C. Lasser and Kenneth H. Lasser as inventors, now abandoned; which claims the benefit of U.S. Provisional Patent Application No. 60/981,093 filed on Oct. 18, 2007, entitled COMPOSITIONS AND METHODS FOR THE TREATMENT OF INFLAMMATORY CONDITIONS, naming Elliott C. Lasser as inventor, now expired, and claims the benefit of U.S. Provisional Patent Application No. 60/914,642 filed on Apr. 27, 2007, entitled COMPOSITIONS AND METHODS FOR THE TREATMENT OF INFLAMMATORY CONDITIONS, naming Elliott C. Lasser as inventor, now expired. The entire content of the foregoing applications is incorporated herein by reference, including all text, tables and drawings.

FIELD

Embodiments of the invention relate to methods and compositions for treating symptoms related to inflammatory conditions and to methods and compositions for treating inflammatory components of a common cold, utilizing various method of administration of X-ray contrast media (CM).

BACKGROUND

Inflammatory conditions afflict large numbers of individuals each year on an acute or chronic basis. While inflammatory responses are usually components of the host's innate immune response, hyperactivity of these responses can result in mild, moderate, or extreme discomfort. Inflammatory conditions include those related to the skin, bronchi, colon, and esophagus, for example. Ongoing research and development efforts have sought anti-inflammatory medications to treat these conditions. Steroid agents and various ephedrine compositions have been effectively used, but with the downside of various adverse side effects and in some cases rebound effects. Non-steroidal anti-inflammatory agents (i.e., NSAIA), antihistamine, recombinant antibodies and other formulations have been used with the hope of reducing the concentration of cytokines and chemokines that produce the irritant effects in moderate and extreme hyper-immune responses. While these have had various degrees of success, they vary in their potential to address issues such as immediacy of effect, cost, and adverse effects. There continues to be a need for simple, cheap, low molecular weight compounds to treat inflammatory conditions and also to treat inflammatory components of the common cold.

SUMMARY

Some embodiments relate to methods of treating a skin inflammatory condition in a mammal in need thereof, which methods can include contacting at least part of the skin of a mammal with a therapeutically effective amount of a composition that includes an X-ray contrast media. The methods further can include, for example, identifying the mammal as a mammal that suffers from a condition related to skin inflammation or dermatitis (e.g., including atopic dermatitis). For example, the condition can be eczema, dermatosis, insect bite reaction, sunburn, inflammation caused by graft v. host disease, inflammation caused by immunobullous disease, other skin allergen reactions, and the like. The skin allergen reaction can be, for example, a reaction resulting from a vaccine, resulting from a sensitizing antigen, and the like. In some aspects the dermatosis can be psoriasis. In some aspects, psoriasis can be specifically excluded from the methods described herein. Also, in some aspects the skin allergen can be, for example, poison ivy, poison oak, poison sumac, grass allergen, dust allergen, pet allergens, and the like. Further, the skin allergen can be a cleaning solution (including e.g., shampoo), a detergent, a cosmetic, a perfume, an industrial chemical, a latex rubber, and the like. In some embodiments, any one or more of the skin inflammatory conditions, skin inflammatory indications listed herein or one or more of the allergens can be specifically excluded from the methods and compositions.

In some embodiments the composition can be formulated as a topical formulation, for example, a gel formulation, a cream formulation, a lotion formulation, a paste formulation, an ointment formulation, an oil formulation, a foam formulation, a shampoo, a soap and the like. In some aspects, the topical compositions can be formulated to be absorbed, including to be substantially absorbed, by an epidermal layer of the skin. For example the topical compositions can include an absorption emollient. The topical formulation further can include, for example, water, petrolatum, glycerin, propylene glycol, benzyl alcohol, magnesium aluminum silicate, and tocopherol linoleate, castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, sodium hyaluronate and the like. Also, in some aspects the topical formulation can include a preservative. For example, the preservative can be at least one of benzalkonium chloride, benzoxonium chloride, benzethonium chloride, cetrimide, sepazonium chloride, cetylpyridinium chloride, domiphen bromide (BRADOSOL®), thimerosal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, PURITE®), POLYQUART®), sodium perborate tetrahydrate, and the like. In some aspects, the topical formulation can include a preservative that can be a quaternary ammonium compound, an alkyl-mercury salt of thiosalicylic acid, a paraben, an alcohol, a biguanide derivative, a stabilized oxychloro complex, a polyglycol-polyamine condensation resin, a stabilized hydrogen peroxide and the like. In some embodiments the quaternary ammonium compound can be a benzalkonium chloride, for example trimethyl benzyl ammonium chloride and the like. In some aspects, one or more of the above-listed ingredients can be specifically excluded from some of the compositions and methods.

Some embodiments relate to methods of treating inflammation of the upper respiratory track/bronchi in a mammal in need thereof, which methods can include contacting at least part of the upper respiratory tract/bronchi of a mammal with a therapeutically effective amount of a composition comprising an X-ray contrast media. The methods further can include, for example, identifying the mammal as a mammal that suffers from a condition related to inflammation of the upper respiratory track/bronchi. For example, the condition can be allergic asthma, allergic bronchitis, asthmatic bronchitis, and bronchoconstriction. In some embodiments, any one or more of the upper respiratory track/bronchi inflammatory conditions listed herein can be specifically excluded from the methods and compositions.

In some embodiments the composition can be formulated as an aerosol formulation. The aerosol formulated can be formulated to be absorbed, including substantially absorbed, by a bronchus. In some aspects, the aerosol composition can include an X-ray contrast media and an aerosolized pharmaceutically acceptable carrier solution or dry powder. For example, the aerosol formulations can include, dichlorodifluoromethane, trichlorofluoromethane, dichlorotetrafluoroethane, or carbon dioxide. The aerosol formulations further can include a preservative. The preservative can be, for example, a quaternary ammonium compound, an alkylmercury salt of thiosalicylic acid, a paraben, an alcohol, a biguanide derivative, a stabilized oxychloro complex, a polyglycol-polyamine condensation resin, a stabilized hydrogen peroxide, and the like. For example, the preservative can be at least one of benzalkonium chloride, benzoxonium chloride, benzethonium chloride, cetrimide, sepazonium chloride, cetylpyridinium chloride, domiphen bromide (BRADOSOL®), thimerosal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, PURITE®), POLYQUART®), sodium perborate tetrahydrate and the like. In some embodiments the quaternary ammonium compound can be a benzalkonium chloride, for example trimethyl benzyl ammonium chloride and the like. In some aspects, the aerosol formulations can be used in a nebulizer. Also, in some aspects, for example, the aerosol formulations can be used in an inhaler. In some aspects, one or more of the above-listed ingredients can be specifically excluded from some of the compositions and methods.

Some embodiments relate to methods of treating a colon inflammatory condition in a mammal in need thereof, which methods can include contacting at least part of the colon of a mammal with a therapeutically effective amount of a composition comprising an X-ray contrast media. The methods further can include, for example, identifying the mammal as a mammal who suffers from a colon inflammatory condition. For example, the condition can be inflammatory bowel disease, irritable bowel syndrome and the like. In some embodiments, any one or more of the colon inflammatory conditions listed herein can be specifically excluded from the methods and compositions.

In some embodiments the composition can be formulated as a rectal formulation. For example as a retention enema. In some aspects, the rectal formulation can be formulated to be absorbed, including partially or substantially absorbed, by the colon. For example, the retention enema can be formulated to be substantially absorbed by the colon. The rectal formulations can further include a preservative. The preservative can include, for example, a quaternary ammonium compound, an alkyl-mercury salt of thiosalicylic acid, a paraben, an alcohol, a biguanide derivative, a stabilized oxychloro complex, a polyglycol-polyamine condensation resin, a stabilized hydrogen peroxide, and the like. For example, the preservative can be at least one of benzalkonium chloride, benzoxonium chloride, benzethonium chloride, cetrimide, sepazonium chloride, cetylpyridinium chloride, domiphen bromide (BRADOSOL®), thimerosal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, PURITE®), POLYQUART®), sodium perborate tetrahydrate and the like. In some embodiments the quaternary ammonium compound can be a benzalkonium chloride, for example trimethyl benzyl ammonium chloride and the like. In some aspects, one or more of the above-listed ingredients can be specifically excluded from some of the compositions and methods.

Some embodiments relate to methods of treating conditions related to inflammation of the esophagus in a mammal in need thereof, which methods can include contacting at least part of the esophagus of the mammal with a therapeutically effective amount of a composition comprising an X-ray contrast media. The conditions can be related to inflammation of the esophagus. For example, the condition can be allergic esophagitis, eosinophilic esophagitis, and the like. In some embodiments, any one or more of the esophageal inflammatory conditions listed herein can be specifically excluded from the methods and compositions.

In some embodiments the composition can be formulated as an oral formulation. For example, the oral formulations can be a liquid, a gel, a syrup, a slurry and the like. Also, in some aspects, the oral formulation can be a spray formulation, a mouth rinse formulation, a mouthwash formulation, a lozenge formulation and the like. The oral formulations can further include a preservative. The preservative can include, for example, a quaternary ammonium compound, an alkyl-mercury salt of thiosalicylic acid, a paraben, an alcohol, a biguanide derivative, a stabilized oxychloro complex, a polyglycol-polyamine condensation resin, a stabilized hydrogen peroxide, and the like. For example, the preservative can be at least one of benzalkonium chloride, benzoxonium chloride, benzethonium chloride, cetrimide, sepazonium chloride, cetylpyridinium chloride, domiphen bromide (BRADOSOL®), thimerosal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, PURITE®), POLYQUART®), sodium perborate tetrahydrate and the like. In some embodiments the quaternary ammonium compound can be a benzalkonium chloride, for example trimethyl benzyl ammonium chloride and the like. In some aspects, one or more of the above-listed ingredients can be specifically excluded from some of the compositions and methods.

In some embodiments, the compositions that include an X-ray contrast media can be contacted with the affected area of the mammal with the composition on a daily basis. Alternatively, in some embodiments, the compositions that include an X-ray contrast media can be contacted with the affected area of the mammal with the composition on an as-needed basis.

In some embodiments, the X-ray contrast media can be a monomeric, dimeric, nonionic, or ionic compound. Further, in some aspects, the X-ray contrast media can be triiodinated, completely or partially substituted, benzene moieties existing in the form of a monomer or a dimer. For example, the X-ray contrast media can be at least one of iopamidol, ioversol, iopromide, iohexol, iothalamate, diatrizoate, ioxaglate, iodipamide, iodixanol, iotrolan, iopanoic acid, tyropanoate (e.g., Na tyropanoate (BILOPAQUE)), and the like. In some aspects of the methods and compositions described herein, any one or more of the listed contrast media can be specifically excluded.

Some embodiments relate to methods of treating a common cold in a mammal in need thereof, which methods can include administering a therapeutically effective amount of a composition that includes an X-ray contrast media. The methods further can include, for example, identifying the mammal as a mammal that suffers from a common cold. In some aspects, treatment of the common cold can include treating a symptom of the common cold. For example, the symptom of the common cold can be a stuffy nose or nasal congestion. Also, in one aspect, the treatment of the common cold does not result in a rebound effect. In some embodiments, the therapeutically effective amount of a composition that includes an X-ray contrast media can be administered as an aerosol formulation. In some embodiments, any one or more of the common cold symptoms or conditions listed herein can be specifically excluded from the methods and compositions.

Some embodiments relate to methods of preparing a composition for treatment of an inflammatory condition or a common cold, which can include contacting an X-ray contrast media with a preservative. The preservative can be at least one of benzalkonium chloride, benzoxonium chloride, benzethonium chloride, cetrimide, sepazonium chloride, cetylpyridinium chloride, domiphen bromide (BRADOSOL®), thimerosal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, PURITE®), POLYQUART®), sodium perborate tetrahydrate and the like. In some aspects, the X-ray contrast media can mixed with the preservative. In some aspects, one or more of the above-listed ingredients can be specifically excluded from some of the compositions and methods. Also, in some aspects the X-ray contrast media and the preservative can be stored in a container. For example, the container can be a spray bottle, a container with a lid and the like.

BRIEF DESCRIPTION OF THE DRAWINGS

FIG. 1 is a photograph of the arm of a human showing the response to injected histamine, dust antigen and grass antigen both with and without pre-treatment with iodipamide.

DETAILED DESCRIPTION

Embodiments disclosed herein relate to the unexpected discovery that X-ray contrast media can be used to treat various inflammatory conditions, including for example, those of the common cold. In some embodiments, the invention relates to methods of treating a condition related to inflammation of the upper respiratory track or bronchi, including the common cold, the skin, the esophagus, and the colon.

Specifically, some embodiments include methods of treating one of these conditions by applying an X-ray contrast media in a manner to contact one or more of the respective inflamed cells or parts of the aforementioned regions. In other embodiments, the invention relates to compositions comprising X-ray contrast media formulated to contact inflamed regions or cells of the skin, upper respiratory track or bronchi, colon, or the esophagus. Also, some embodiments relate to the use of X-ray contrast media to treat the common cold. Specifically, some embodiments relate to compositions, including a topical composition, an aerosolized composition, an enema composition, or an oral composition comprising an X-ray contrast media. In some aspects, any one or more of the contrast media can be specifically excluded in the methods and compositions described herein.

X-ray contrast media (CM) can be used to treat and provide relief of symptoms in the spectrum of inflammatory and hypersensitivity conditions that include conditions of the skin, esophagus, colon, bronchi/upper respiratory tract, certain neoplasms, and the common cold. Many of these conditions are associated with the activity of mast cells. The triggering of mast cells leads to degranulation and the release of preformed mediators. Surprisingly, CM can inhibit mast cell activation. It is not believed that any other drugs have a similar totipotential capacity as seen with CM. This potential permits the contrast media to be applied in a number of ways that permit inhibition of mast cells. These cells, when activated, are increasingly recognized to participate in a large number of inflammatory conditions. Furthermore, CM can function as general enzyme inhibitors, including at concentrations attainable with topical application. Also, CM can act as effective inhibitors of various enzymes, including against adenosine triphosphate, carbonic anhydrase, and angiotensin converting enzyme, alcohol dehydrogenase, and beta-glucuronidase, even at topical concentrations. These attributes permit the CM to function as potent anti-inflammatories and to be effective at treating or minimizing various disease conditions and neoplasms.

X-Ray Contrast Media

X-ray contrast media have been used for many years in the field of radiology. While the molecules have assumed some structural differences over the years, the basic concept that iodine attached to organic ring structures will impair x-ray penetration remains the same. The x-ray molecules, referred to as "contrast media" have been used to opacify blood vessels, organs, and other parts of the body that have orifices leading externally or are amenable to needle injection.

X-ray contrast media today are generally triiodinated, completely or incompletely substituted, benzene moieties existing in the form of a monomer or a dimer. These contrast media molecules can be either ionic or nonionic (or in the case of one dimer, part ionic and part nonionic). Generally, there can be slight variations in the amide side chains attached at the 3 and 5 positions on the ring and in the nature of the cations (for the ionic media) and there can be slight differences in the length of the aliphatic chains linking the dimers and in the nature of the coupler group.

Some examples of X-ray contrast media that are commercially available today are iopadmidol, ioversol, iopromide, and iohexol which are nonionic monomers. Iothalamate and diatrizoate are ionic monomers. Ioxaglate and iodipamide are ionic dimers, while iodixanol and iotrolan are nonionic dimers.

Surprisingly, X-ray contrast media have now been discovered as disclosed herein to be useful for treating inflammatory conditions of the skin, the bronchi, the esophagus and the colon. Any X-ray contrast media can be used in the methods and compositions described herein, including for example, iopamidol, ioversol, iopromide, iohexol, iothalamate, diatrizoate, ioxaglate, iodipamide, iodixanol, iopanoic acid, sodium tyropanoate (BILOPAQUE) and iotrolan. Any one of the contrast media described herein can be specifically excluded from the methods and compositions described herein.

Patient Identification

Compositions described herein can be administered to a subject experiencing or at risk of experiencing a condition related to inflammation and/or related to the common cold. The patient subject can be selected from a variety of mammals including mice; rats; rabbits; guinea pigs; dogs; cats; sheep; goats; cows; horses; pigs; primates, such as monkeys, chimpanzees, and apes; and humans.

In some embodiments, the patient can be one who has never experienced an inflammatory reaction. In other embodiments, the patient can have experienced at least one or more inflammatory reactions. The patient can also experience inflammatory reactions that may or may not be triggered by known allergens. In some embodiments, the inflammatory reaction can be a reaction to a skin allergen, such as a cleaning solution, a detergent, a cosmetic, a soap or shampoo, a medication, a sun block, a lotion, a perfume, an industrial chemical, a latex rubber, a dust allergen, a grass allergen, a cat allergen or a component therein, or the skin allergen can be poison ivy, poison oak, or poison sumac. In some embodiments, one or more of the allergens can be excluded from the methods described herein.

In some embodiments, patients can be identified for the methods described herein by the observation of symptoms related to inflammation. In other embodiments, patients can be predisposed to a condition related to inflammation, for example, due to a genetic predisposition or due to the occurrence of a related condition. In still other embodiments, clinical tests, such as allergy tests, can identify patients for the methods described herein.

In some embodiments, a patient can have or be at risk of having a cold. The cold may be a common cold produced by a number of different viruses. The cold may include nasal symptoms, such as a runny nose, nasal congestion or cough.

Furthermore, in some embodiments, the patient may be suffering from or at risk for a condition related to immune cell activation due to the conversion of angiotensin-I to angiotensin-II. In some aspects the contrast media can be used to inhibit the conversion, thereby reducing the immune cell activation that can lead to inflammation.

Methods and Compositions

In some embodiments, methods herein relate to methods of treating a patient suffering from or at risk of suffering from a condition which is related to inflammation. In some embodiments, the condition related to inflammation can be attributable to hyperactivity of an immune cell. In other embodiments, multiple types of immune cells may be hyperactive. In still other embodiments, the invention relates to compositions specifically formulated to treat specific immune cells or immune cells located in particular regions of the body. In some embodiments, the contrast media can include one or more of the contrast media described herein. In some aspects of the embodiments, one or more of the contrast media described herein can be excluded. In some embodiments, any one of the specific indications described below can be specifically excluded.

Skin Immune Cells and Skin Inflammatory Conditions

Certain immune cells of the skin may differ in their morphology, histochemical properties, and functional properties from other immune cells. Additionally, immune cells of the skin may be deep in the tissue compared to other immune cells. Surprisingly, some embodiments are based upon the surprising discovery that contrast media can have efficacy against skin inflammatory conditions.

Some embodiments relate to compositions comprising an X-ray contrast media that can be used to treat or inhibit inflammatory conditions of the skin. In some embodiments, the compositions can include a topical carrier such as an emollient and an X-ray contrast media that can be used to treat inflammatory conditions of the skin. The topical carrier can increase the percutaneous absorption of the composition. Although any CM can be used, in some preferred aspects, lipophilic CM such as the ionic dimer iodipamide can be used. Emollients can be used to further improve absorption and penetration of the CM. For example, iodixanol, a hydrophilic CM, can be formulated with an excipient/emollient in order to improve skin absorption. In some aspects of the methods for treatment or inhibition of inflammatory conditions of the skin, one or more of the CM described herein can be specifically excluded.

In some embodiments, methods described herein can be used to treat conditions related to inflammation. These conditions can include eczema, dermatitis, dermatosis, inflammation caused by graft v. host disease, inflammation caused by immunobullous disease, an insect bite reaction, a sunburn or a skin allergen reaction. The skin allergen can be, for example, a shampoo or perfume or a component therein or the skin allergen can be latex, poison ivy, poison oak, poison sumac, a dust allergen, a grass allergen, or a pet allergen, e.g., a cat allergen or the like. The dermatosis can be psoriasis or atopic dermatitis. In some embodiments, any one or more of the skin inflammatory conditions listed herein can be specifically excluded from the methods and compositions.

Also, the injection of an allergen or vaccine can provoke a hyperimmune (anaphylactic) reaction. Some embodiments relate to concomitant intradermal or subdermal injections CM in sufficient concentrations at the site of the concomitant injection in order to reduce or prevent the hyperimmune reaction. In some embodiments, any one or more of the skin inflammatory conditions listed herein can be specifically excluded from the methods and compositions.

The inhibitory effects of X-ray contrast materials (CM) on mast cells and the array of immune cells permits CM to have efficacy in a wide variety of inflammatory skin conditions. In addition to atopic dermatitis, several other pruritic skin conditions including prurigo nodularis, papular urticaria, and pruritis vulvae can be treated with CM. Also, CM can be used to treat allergic contact dermatitis, latex allergy, and irritant contact dermatitis. Mast cells, in part by elaboration of tumor necrosis factor (TNF), contribute to the expression of certain models of contact hypersensitivity. See Suto H, Nakae S, Kakurai M, Sedgwick J D, Tsai M, Galli S J. Mast cell associated TNF promotes dendritic cell migration. J. Immunol. 2006 Apr. 1; 176(7): 4102-12, which is incorporated herein by reference in its entirety, in particular (without being limited thereto), for the inflammatory conditions or mechanisms that can be minimized or treated with CM.

In psoriasis, known mediators of inflammation include dendritic cells, Langerhans cells, T-lymphocytes, and mast cells, which are thought to be a primary source of TNF that is overexpressed and important in the pathophysiology of the disease (Kawaguchi M, Mitsuhashi Y, Kondo S. Overexpression of tumor necrosis factor-alpha-converting enzyme in psoriasis. Br J. Dermatol. 2005 May; 152(5): 915-9, which is incorporated herein by reference in its entirety, in particular (without being limited thereto), for the inflammatory conditions or mechanisms that can be minimized or treated with CM). Other similar papulo-squamous dermatoses including pityriasis rosea and lichen planus can be treated with topical CM.

CM can be used to treat sclerosing dermatoses, including scleroderma, morphea, and lichen sclerosis. Sclerosing dermatoses, including scleroderma, morphea, and lichen sclerosis are characterized by increased dermal collagen, thought to be related to increased mast cells and histamine effects (Falanga V, Soter N A, Altman R D, Kerdal F A. Elevated plasma histamine levels in systemic sclerosis (Scleroderma). Arch Dermatol. 1990 March; 126(3):336-8; which is incorporated herein by reference in its entirety, in particular (without being limited thereto), for the inflammatory conditions or mechanisms that can be minimized or treated with CM), and are candidates for application of topical CM therapy.

Bronchial Immune Cells and Bronchial Inflammatory Conditions

Certain bronchial immune cells can differ from other immune cells by closer proximity to the airway. Bronchial immune cells can also differ from other immune cells by the types of mediators they release. The density of bronchial immune cells can be higher than other immune cells. The results of immune cell release in the bronchii can include bronchospasm and mucus production. Surprisingly, contrast media can contact the cells of the bronchii and come into proximity with immune cells involved in an inflammatory condition.

Some embodiments relate to compositions comprising an X-ray contrast media that can be used to treat or inhibit inflammatory conditions of the bronchii. In some embodiments, the compositions can include a carrier and an X-ray contrast media. The carrier can affect the solubility and/or the diffusivity of the composition compared to the solubility and/or the diffusivity of the X-ray contrast media. Some other embodiments relate to aerosolized compositions comprising an X-ray contrast media. The aerosolized compositions can provide a mechanism of obtaining a high surface area of contact between the composition and the upper airway system. In other embodiments, the formulation can be an inhaled powder cut in such a fashion that it will be predisposed to coat the bronchi rather than areas higher or lower in the respiratory system and will not be itself an irritant.

Accordingly, some embodiments relate to methods and compositions to treat a conditions resulting from bronchial immune cell hyperactivity or related to a bronchial inflammatory condition. The condition can be, for example, asthma, bronchitis including allergic or asthmatic bronchitis, or bronchoconstriction. In some aspects, any one of the contrast media described herein can be specifically excluded from the methods and compositions. Also, in some embodiments, any one or more of the bronchi/respiratory inflammatory conditions listed herein can be specifically excluded from the methods and compositions.

Colon Immune Cells and Colon Inflammatory Conditions

Certain colon immune cells can differ from other immune cells. Colon immune cells can be located in the epithelial or subepithelial layers of the colon. Surprisingly, contrast media given in a retention enema can permeate epithelial cells and can also gain entrance to the intercellular space giving proximity to the immune cells.

Some embodiments relate to compositions comprising an X-ray contrast media that can be used to treat or inhibit inflammatory conditions of the colon. In some embodiments, the compositions can include an enema composition comprising an X-ray contrast media. The composition can also comprise a carrier. The carrier can affect the solubility and/or the diffusivity of the composition compared to the solubility and/or the diffusivity of the X-ray contrast media. The carrier can also comprise a suspending or thickening agent to prolong release of the X-ray contrast media.

Accordingly, some embodiments relate to methods and compositions to treat a condition related to colon immune cell hyperactivity or related to a colon inflammatory condition. These conditions can include, for example, inflammatory bowel disease, irritable bowel syndrome, and ulcerative colitis. In some aspects, any one of the contrast media described herein can be specifically excluded from the methods and compositions. Also, in some embodiments, any one or more of the colon inflammatory conditions listed herein can be specifically excluded from the methods and compositions.

Esophageal Immune Cells and Esophageal Inflammatory Conditions

Certain esophageal immune cells can differ from other immune cells. Esophageal immune cells can be located in the lamina propria, the deep submucosa, and/or the muscularis propria of the esophagus. Surprisingly, some embodiments relate to the surprising discovery that X-ray contrast media can treat inflammatory conditions of the esophagus.

Some embodiments relate to compositions comprising an X-ray contrast media that can be used to treat or inhibit inflammatory conditions of the esophagus. In some embodiments, the compositions can include oral compositions comprising an X-ray contrast media. The oral composition can include, for example, a carrier that improves the absorption of the composition through the esophagus, for example, as compared to the absorption of the certain X-ray contrast media alone. The oral composition can also include a thickener that prolongs the transit of the contrast media through the esophagus, for example.

Accordingly, some embodiments relate to compositions and methods that can be used to treat a condition related to esophagus immune cell hyperactivity or related to an esophageal inflammatory condition. The condition can be, for example, esophagitis including allergic esophagitis. In some aspects, any one of the contrast media described herein can be specifically excluded from the methods and compositions. Also, in some embodiments, any one or more of the esophageal inflammatory conditions listed herein can be specifically excluded from the methods and compositions.

Common Cold

Common colds can include a variety of symptoms, including a blocked/stuffy nose, a runny nose, and a cough. Many cold medicines currently marketed to relieve a blocked nose comprise ephedrine. Such medications can be associated with a "rebound effect." A rebound effect can occur by overusing a nasal spray decongestant such that the blood vessels in the nose swell, resulting in worsened symptoms. Meanwhile, other treatments, such as corticosteroids, antihistamines and cromoglycates, appear incompletely effective in relieving the blocked nose symptom. Further, common cold medicines can be associated with side effects, such as drowsiness and nasal irritation. Surprisingly, some embodiments relate to the surprising discovery that X-ray contrast media can treat cold symptoms, including inflammatory conditions associated with the common cold.

Some embodiments relate to compositions comprising an X-ray contrast media that can be used to treat the common cold or a symptom of the common cold, such as a stuffy nose. The composition for example can relieve or partially relieve a symptom of the cold. The composition can reduce the duration of the cold. In some aspects, any one of the contrast media described herein can be specifically excluded from the methods and compositions. Also, in some embodiments, any one or more of the cold conditions or symptoms listed herein can be specifically excluded from the methods and compositions Though not wishing to be bound by any particular theory, it is likely that the mechanism of action involves inhibition of angiotensin converting enzyme (ACE), inhibition of mast cell activity, general enzyme inhibitory effects, and antihistaminic effects. Ace is responsible for the conversion of angiotensin Ito angiotensin II, the latter of which is an activator of the innate immune response expressed by activated macrophages and T-cells. Immune cells, including macrophages, T-cells and B-cells and neutrophils, contain receptors for angiotensin 2. Viral-induced activation of these cells in the nasal submucosa can produce some of the mediators responsible for the symptoms of the "cold." Some embodiments relate to methods of inhibiting angiotensin converting enzyme, for example, in a patient suffering from or susceptible to a condition described herein or any other condition caused by or contributed to by the conversion of angiotensin Ito angiotensin II. The methods can include the identification of such a patient.

Treatment of Neoplasms and Other Conditions

Some embodiments relate to the use of X-ray contrast materials for the treatment of neoplasms or cancers, in particular those cancers or neoplasms where mast cells contribute to the disease condition and progression.

The inhibition of angiogenic molecules from mast cells including angiopoietin, heparin, interleukin-8, and vascular endothelial growth factor can promote cancer cell death. Angiogenesis can play a role in human lymphoproliferative disease, including cutaneous T-cell lymphoma and mycosis fungoides (Mazur, G). The latter is a slowly progressive skin based lymphoma which, at least initially, is treated by skin based therapies. Some embodiments relate to topical application of contrast media to inhibit the inflammatory and angiogenic process that supports cutaneous lymphoma progression. Thus topical application of CM can impede tumor growth of several different kinds. See Mazur, G et al, Pathol Oncol Res. 2004; 10(1): 34-36 Epub 2004 Mar. 18, which is incorporated herein by reference in its entirety, and particularly incorporated for several examples of disease conditions that can be treated using CM.

Some embodiments relate to the use of X-ray contrast materials for the treatment of pancreatic neoplasms, such as pancreatic ductal adenocarcinomas. The release of some substances from activated mast cells may play a role in the production of pancreatic ductal adenocarcinomas. For example, the mast cells may contribute to angiogenesis or macroscopic expansion of pancreatic islet tumors. Surprisingly, X-ray contrast media can inhibit activation of mast cells in pancreatic tissue. Thus, in some aspects, one or more X-ray contrast materials can be contacted with the pancreatic duct, for example, via a catheter or by injection to inhibit the mast cells and thereby inhibit the growth of pancreatic carcinomas. For example, the pancreatic cells can be washed over by the CM in order to treat the pancreatic adenocarcinoma. Again, the CM can be administered by any route or means that permits contact of the CM with the cells. Preferably, the CM can be administered via catheter, via intraperitoneal injection or by suffusing the pancreas via injections into the arterial system leading the pancreas.

Route of Administration and Formulation

The exact formulation and route of administration for the compositions described herein can be chosen by the individual physician in view of the patient's condition. See e.g., Fingl et al. 1975, in "The Pharmacological Basis of Therapeutics," Ch. 1 p. 1; which is incorporated herein by reference in its entirety. As set forth more fully below, preferred routes of administration include, for example, topical, oral, rectal, parenteral delivery (including intramuscular, subcutaneous, injections), as well as, intranasal, or ocular injections. As mentioned above, U.S. Provisional Application Ser. No. 60/914,642, filed on Apr. 27, 2007, and U.S. Provisional Application Ser. No. 60/981,093, filed on Nov. 28, 2007 by Elliott C. Lasser and both entitled "COMPOSITIONS AND METHODS FOR THE TREATMENT OF INFLAMMATORY CONDITIONS," are each incorporated herein by reference in their entirety. In particular, the appendix to the specification (Remington's Pharmaceutical Sciences) is incorporated herein for all of the various formulations, ingredients, excipients, etc., listed therein. The various X-ray contrast materials listed herein, alone or in combination, can be incorporated into or used with the materials described in Remington's.

Alternately, one can administer the compound in a local rather than systemic manner, for example, via direct application to the skin or region of interest for treating, including using a depot or sustained release formulation. Furthermore, one can administer the drug in a targeted drug delivery system, for example, in a liposome coated with a tissue-specific antibody. The liposomes will be targeted to and taken up selectively by the organ or cells of the desired region.

In some embodiments, the contrast media can be administered alone. In other embodiments, the contrast media can be administered in combination with one or more additional materials, for example, as two separate compositions or as a single composition where the additional material(s) is (are) mixed or formulated together with the contrast media. For example, without being limited thereto, the contrast media can be formulated with additional excipients, additional active ingredients, other contrast media. In some aspects, when administered in the forms described herein the contrast media can attain concentrations at a target tissue such as the nose, the eye, the bronchi, the skin, etc. that cannot be attained by the usual intravascular administration of the contrast material.

The pharmaceutical compositions can be manufactured by any suitable manner, including, e.g., by means of conventional mixing, dissolving, granulating, dragee-making, levigating, emulsifying, encapsulating, entrapping or tableting processes.

Pharmaceutical compositions for use in accordance with the invention thus can be formulated in any suitable manner using one or more physiologically acceptable carriers comprising excipients and auxiliaries which facilitate processing of the active compounds into preparations which can be used pharmaceutically. Proper formulation can depend upon the route of administration chosen. Any suitable techniques, carriers, and excipients can be used, including those understood in the art; e.g., in Remington's Pharmaceutical Sciences, above. The attached pages 1523-1553 from Remington's Pharmaceutical Sciences are incorporated herein by reference in their entirety.

Topical Formulations

Compositions comprising an X-ray contrast media can be, in some embodiments, topical compositions. The topical composition can be formulated such that the X-ray contrast media is absorbed, including substantially absorbed, percutaneously. The topical composition can be formulated to increase the probability that the X-ray contrast media of the composition will contact inflamed tissues and immune cells.

The composition can comprise a carrier. The carrier can improve the absorption of the composition as compared to the absorption of the X-ray contrast media alone. The composition can include, for example, a penetration enhancing agent such as dimethylsulfoxide, propylene glycol, AZONE™, and the like.

Carriers are further described below. However, in some embodiments, the carrier can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

The topical formulation can be the contrast media alone, or the contrast media in combination with a gel, a cream, a lotion, a paste, an ointment, an oil, or a foam. The topical composition can be combined with other topical compositions, such as shampoo. Additionally, a multitude of appropriate topical compositions can be utilized. See e.g., Blaug, in "Remington's Pharmaceutical Sciences" Mack publishing Company, Easton Pa., 15th edition, 1975, Ch. 87 which is incorporated herein by reference in its entirety. These compositions include, for example, powders, pastes, ointments, jelly, waxes, oils, lipids, anhydrous absorption bases, oil-in water or water-in-oil emulsions, emulsions carbowax (polyethylene glycols of a variety of molecular weights), semi-solid gels, semi-solid mixtures containing carbowax, and the like.

Aerosolized Formulations

Compositions comprising an X-ray contrast media can be, in some embodiments, aerosolized compositions. The aerosolized composition can be formulated such that the composition has increased solubility and/or diffusivity. The aerosolized composition can be formulated to increase the probability that the X-ray contrast media of the composition will contact bronchial inflammation and/or immune cells. The composition can comprise a carrier. The carrier can improve the absorption of the composition, change the viscosity of the composition, change the solubility of the composition, or change the diffusivity of the composition as compared to that of the X-ray contrast media alone.

Liquid pharmaceutically administrable compositions can, for example, be prepared by dissolving, dispersing, etc. an X-ray contrast media as defined above and optional pharmaceutical adjuvants in a carrier (e.g., water, saline, aqueous dextrose, glycerol, glycols, ethanol or the like) to form a solution or suspension. Solutions to be aerosolized can be prepared in any suitable form, for example, either as liquid solutions or suspensions, as emulsions, or in solid forms suitable for dissolution or suspension in liquid prior to aerosol production and inhalation.

For administration by inhalation, the compositions described herein can conveniently be delivered in the form of an aerosol (e.g., through liquid nebulization, dry powder dispersion or meter-dose administration The aerosol can be delivered from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

By non-limiting example water-based liquid formulations can include an X-ray contrast media alone or with non-encapsulating water soluble excipients. Simple formulations can also include organic-based liquid formulations for nebulization or meter-dose inhaler. By non-limiting example organic-based liquid formulations can include an X-ray contrast media or with non-encapsulating organic soluble excipients.

Simple formulations can also include dry powder formulations for administration with a dry powder inhaler. By non-limiting example dry powder formulations can include an X-ray contrast media alone or with either water soluble or organic soluble non-encapsulating excipients with or without a blending agent such as lactose.

Formulations can include water-based liquid formulations for nebulization. A non-limiting example water-based liquid complex formulations can include X-ray contrast media encapsulated or complexed with water-soluble excipients such as lipids, liposomes, cyclodextrins, microencapsulations, and emulsions.

Formulations can also include organic-based liquid formulations for nebulization or meter-dose inhaler. A non-limiting example organic-based liquid complex formulations can include X-ray contrast media encapsulated or complexed with organic-soluble excipients such as lipids, microencapsulations, and reverse-phase water-based emulsions.

Formulations can also include low-solubility, water-based liquid formulations for nebulization. A non-limiting example low-solubility, water-based liquid complex formulations can include X-ray contrast media as a low-water soluble, stable nanosuspension alone or in co-crystal/co-precipitate excipient complexes, or mixtures with low solubility lipids, such as lipid nanosuspensions.

Formulations can also include low-solubility, organic-based liquid formulations for nebulization or meter-dose inhaler. A non-limiting example low-solubility, organic-based liquid complex formulations can include X-ray contrast media as a low-organic soluble, stable nanosuspension alone or in co-crystal/co-precipitate excipient complexes, or mixtures with low solubility lipids, such as lipid nanosuspensions.

Formulations can also include dry powder formulations for administration using a dry powder inhaler. A non-limiting example, complex dry powder formulations can include X-ray contrast media in co-crystal/co-precipitate/spray dried complex or mixture with low-water soluble excipients/salts in dry powder form with or without a blending agent such as lactose.

Specific methods for simple and complex formulation preparation are described herein. Any suitable X-ray contrast media, including those described herein, are preferably directly administered as an aerosol to the respiratory tract.

Any suitable device technology can be used to deliver, for example, a dry powder or a liquid aerosolized product comprising an X-ray contrast material. Dry powder formulations in some circumstances can require less time for drug administration. Liquid formulations can have longer administration times.

For aqueous and other non-pressurized liquid systems, a variety of nebulizers (including small volume nebulizers) can be used to aerosolize the formulations. Compressor-driven nebulizers can utilize jet technology and can use compressed air to generate the liquid aerosol. Such devices are commercially available from, for example, Healthdyne Technologies, Inc.; Invacare, Inc.; Mountain Medical Equipment, Inc.; Pan Respiratory, Inc.; Mada Medical, Inc.; Puritan-Bennet; Schuco, Inc.; DeVilbiss Health Care, Inc.; and Hospitak, Inc. Ultrasonic nebulizers generally rely on mechanical energy in the form of vibration of a piezoelectric crystal to generate respirable liquid droplets and are commercially available from, for example, Omron Heathcare, Inc. and DeVilbiss Health Care, Inc. Vibrating mesh nebulizers rely upon either piezoelectric or mechanical pulses to respirable liquid droplets generate Commercial examples of nebulizers that RESPIRGARD II®, AERONEB®, AERONEB® Pro, and AERONEB® Go produced by Aerogen; AERX® and AERX ESSENCE™ produced by Aradigm; PORTA-NEB®, FREEWAY FREEDOM™, Sidestream, Ventstream and I-neb produced by Respironics, Inc.; and PARI LC-PLUS®, PARI LC-STAR®, and e-Flow7m produced by PARI, GmbH. By further non-limiting example, U.S. Pat. No. 6,196,219, is hereby incorporated by reference in its entirety.

In some embodiments, the drug solution can be formed prior to use of the nebulizer by a patient. In other embodiments, the drug can be stored in the nebulizer in solid form. In this case, the solution can be mixed upon activation of the nebulizer, such as described in U.S. Pat. No. 6,427,682 and PCT Publication No. WO 03/035030, both of which are hereby incorporated by reference in their entirety. In these nebulizers, the drug, optionally combined with excipients to form a solid composition, can be stored in a separate compartment from a liquid solvent.

Enema Formulations

Compositions comprising an X-ray contrast media can be, in some embodiments, enema compositions. The enema composition can be formulated such that the composition has different solubility and/or diffusivity than the X-ray contrast media alone. The enema composition can be formulated to increase the probability that the X-ray contrast media of the composition will contact colon inflammatory condition and/or immune cells. The composition can comprise a carrier. The carrier can improve the absorption of the composition, change the viscosity of the composition, change the solubility of the composition, or change the diffusivity of the composition as compared to that of the X-ray contrast media alone.

The compositions can also be formulated in rectal compositions such as suppositories or retention enemas, e.g., containing suitable suppository bases such as cocoa butter or other glycerides. Retention enema preparations or solutions for rectal or colonic irrigation can be the active ingredient alone or can be made by combining the active ingredient with a pharmaceutically acceptable liquid carrier. The carrier vehicle can be a natural or synthetic thickener such as gums, acrylates or modified celluloses. The formulation can also comprise an effective amount of a lubricant such as a natural or synthetic fat or oil, e.g., a tris-fatty acid glycerate or lecithin. Nontoxic nonionic surfactants can also be included as wetting agents and dispersants. Unit dosages of enema formulations can be administered from prefilled bags or syringes. The carrier vehicle can also comprise an effective amount of a foaming agent such as n-butane, propane or i-butane. Such formulations can be delivered from a preloaded syringe pressurized container, so that the vehicle is delivered to the colon as a foam, which inhibits its escape from the target site. As is well known in the art, enema preparations can be administered using, and can be packaged within, a delivery device adapted to the rectal anatomy of the subject.

Oral Formulations

Compositions comprising an X-ray contrast media can be, in some embodiments, oral compositions. The oral composition can be formulated such that the composition has different solubility and/or diffusivity than the X-ray contrast media alone. The oral composition can be formulated to increase the probability that the X-ray contrast media of the composition will contact esophageal inflammatory conditions and/or immune cells. The composition can comprise a carrier. The carrier can change the absorption of the composition, change the viscosity of the composition, change the solubility of the composition, or change the diffusivity of the composition as compared to that of the X-ray contrast media.

In some aspects, the X-ray contrast media can be used alone or can be formulated readily by combining the active compounds with pharmaceutically acceptable carriers well known in the art. Such carriers enable the contrast media to be formulated as liquids, gels, syrups, slurries, suspensions and the like, for oral ingestion by a patient to be treated. In some embodiments, oral compositions can be formulated as a spray, a mouth rinse, a mouthwash, and a lozenge. are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropyl methylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

The compositions described herein can be included in a food or beverage product. In some preferred embodiments, the compositions can be included in a food or beverage product similar to the craved substance. The food or beverage product can be a beverage, a soup, a solid, a semi-solid, or a frozen confection. The beverage can be a still beverage or a carbonated beverage, and moreover, can be a suspension, for example, a shake, frappe, or float. Both carbonated and non-carbonated beverages can be "diet" beverages made with low calorie or no-calorie sweeteners, including saccharine, aspartame, dihydrochalcones, monellin, steviosides, glycyrrhizin, sorbitol, mannitol, maltitol, and others. The beverage can be an infusion or extract, including a tea or a coffee. The contrast media can also be in a powder form. Preferably the powder is free-flowing and readily mixable with water or other fluid. The powder can be mixed with a variety of fluids. Thus, for example, the powder form can be mixed with water, soda, diet soda, tea, coffee, fruit juice, diet fruit juice, flavored diet beverages, and the like. Preferably, the powder form can be mixed with water or other fluid before drinking. In some embodiments, the contrast media can be delivered in the form of a toothpaste.

The compositions described herein can be formulated as a solution preconcentrate; i.e., a composition intended to be dispersed with water, either prior to administration in the form of a drink, or dispersed in vivo. The composition can be provided in the form of a diluted preconcentrate (i.e., an aqueous dispersion), a semi-solid dispersion or a solid dispersion.

For transmucosal administration, penetrants appropriate to the barrier to be permeated can be used in the formulation. Such penetrants are generally known in the art.

For intradermal or subdermal injections standard needle and syringe techniques can be used.

Pharmaceutical Carriers

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism. In some embodiments, a pharmaceutical carrier for a composition described herein can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant POLYSORBATE 80™, and 65% w/v polyethylene glycol 300, made up to volume in absolute ethanol. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of POLYSORBATE 80™; the fraction size of polyethylene glycol can be varied; other biocompatible polymers can replace polyethylene glycol, e.g., polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity. Additionally, the compounds can be delivered using a sustained-release system, such as semipermeable matrices of solid hydrophobic polymers containing the therapeutic agent. The pharmaceutical compositions described herein can be administered to a patient per se, or in pharmaceutical compositions where they are mixed with other active ingredients, as in combination therapy, or suitable carriers or excipient(s). The compounds and compositions can be formulated with salts or excipients, such as for example, sodium or meglumine. Techniques for formulation and administration of the compounds of the instant application can be found in "Remington's Pharmaceutical Sciences," Mack Publishing Co., Easton, Pa., 18th edition, 1990.

Furthermore, the compounds and compositions used herein can preferably be stable over an extended period of time, for example on the order of months or years. Compositions comprising an X-ray contrast media can, in some embodiments, comprise a preservative. The preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). The preservative can comprise an alkyl-mercury salt of thiosalicylic acid, such as thimerosal, phenylmercuric nitrate, phenylmercuric acetate or phenylmercuric borate. The preservative can comprise a parabens, such as methylparaben or propylparaben. The preservative can comprise an alcohol, such as chlorobutanol, benzyl alcohol or phenyl ethyl alcohol. The preservative can comprise a biguanide derivative, such as chlorohexidine or polyhexamethylene biguanide. The preservative can comprise sodium perborate, imidazolidinyl urea, and/or sorbic acid. The preservative can comprise stabilized oxychloro complexes, such as known and commercially available under the trade name PURITE®). The preservative can comprise polyglycol-polyamine condensation resins, such as known and commercially available under the trade name POLYQUART®). from Henkel KGaA. The preservative can comprise stabilized hydrogen peroxide generated from a source of hydrogen peroxide for providing an effective trace amount of resultant hydrogen peroxide, such as sodium perborate tetrahydrate. The preservative can be benzalkonium chloride.

The preservative can enable a composition comprising an X-ray contrast media to be used on multiple occasions. The preservative can reduce the effects of one or more of acid exposure, base exposure, air exposure, heat, and light on the X-ray contrast media. The compounds and compositions used herein can include any suitable buffers, such as for example, sodium citrate buffer and/or sequestering agents, such as edetate di sodium sequestering agent. Ingredients, such as meglumine, may be added to adjust the pH of a composition or compound described herein. Compounds and compositions described herein may comprise sodium and/or iodine, such as organically bound iodine. Compositions and compounds used herein may be provided in a container in which the air is replaced by another substance, such as nitrogen.

Dosages

Pharmaceutical compositions suitable for use in the invention include compositions where the active ingredients are contained in an amount effective to achieve its intended purpose. A "therapeutically effective amount" means an amount to treat or inhibit a symptom related to the specific inflammatory condition or related to the particular immune cell hyperactivity. The symptom can be a symptom already occurring or expected to occur. In some embodiments, the symptom can be inflammation, swelling or redness. In some embodiments, the symptom is erythema and swelling that is provoked by an allergen, such as a skin allergen. Determination of a therapeutically effective amount is well within the capability of those skilled in the art, especially in light of the detailed disclosure provided herein.

In other embodiments, a therapeutically effective amount can describe the amount necessary for a significant quantity of the composition to contact the desired region or immune cells.

Within certain embodiments of the invention, dosages of administered contrast media can be from 0.01-0.1 grams, 0.1-5 grams, 5-10 grams, 10-15 grams, 15-20 grams, 20-25 grams, 25-30 grams, 30-35 grams, 35-40 grains, 40-45 grams, 45-50 grams and 50-200 grams.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions comprising a compound of the invention formulated in a compatible pharmaceutical carrier can also be prepared, placed in an appropriate container, and labeled for treatment of an indicated condition.

It will be understood by those of skill in the art that numerous and various modifications can be made without departing from the spirit of the invention. Therefore, it should be clearly understood that the forms of the invention are illustrative only and are not intended to limit the scope of the invention.

EXAMPLES

Example 1

The patient suffers from an inflammatory condition related to the skin. At the time of consultation, he is otherwise healthy. He is prescribed a topical composition comprising an X-ray contrast media. Follow up reveals that the administration of the composition improves the condition.

Example 2

The patient suffers from eczema or psoriasis. At the time of consultation, he is otherwise healthy. He is prescribed a topical composition comprising an X-ray contrast media and an emollient. Follow up reveals that the administration of the composition improves the eczema or psoriasis.

Example 3

The patient suffers from a condition related to bronchial inflammation. At the time of consultation, he is otherwise healthy. He is prescribed an aerosolized composition comprising an X-ray contrast media. Follow up reveals that the administration of the composition improves the condition.

Example 4

The patient suffers from allergic esophagitis. At the time of consultation, he is otherwise healthy. He is prescribed an oral composition comprising an X-ray contrast media. Follow up reveals that the administration of the composition improves the allergic esophagitis.

Example 5

The patient suffers from a condition related to colon inflammation such as ulcerative colitis. At the time of consultation, she is otherwise healthy. She is prescribed an enema composition comprising an X-ray contrast media. Follow up reveals that the administration of the composition improves the condition.

Example 6

The patient suffers from inflammatory bowel disease such as irritable bowel syndrome. At the time of consultation, she is otherwise healthy. She is prescribed an enema composition comprising an X-ray contrast media. Follow up reveals that the administration of the composition improves the inflammatory bowel disease.

Example 7

The patient suffers from allergic esophagitis. At the time of consultation, she is otherwise healthy. She is prescribed an oral composition comprising an X-ray contrast media. Follow up reveals that the administration of the composition improves the allergic esophagitis.

Example 8

The patient suffers from a common cold. At the time of consultation, she is otherwise healthy. She is prescribed a nasal composition comprising an X-ray contrast media. Follow up reveals that the administration of the composition improves the cold.

Example 9

The patient suffers from nasal congestion of undetermined origin. At the time of consultation, she is otherwise healthy. She is prescribed a nasal composition comprising an X-ray contrast media. Follow up reveals that the administration of the composition improves the nasal congestion.

Example 10

The patient is known to have anaphylactic symptoms on injection of vaccines or sensitizing antigens in desensitization procedures. He is prescribed a subdermal contrast media injection along with the sensitizing antigen or vaccine. Follow up reveals that the administration of the composition inhibits the vaccine reaction or the anaphylactic reaction.

Example 11

A single-blind study was conducted using three human patients. The patients were exposed to cat allergen at three different dilutions, 1:1,000, 1:100, and 1:10. Exposure to the 1:1,000 dilution of allergen was showed no symptoms in the patients. Exposure to the 1:100 dilution of allergen caused a mild reaction in all of the patients. Exposure to the 1:10 dilution of allergen caused moderate reactions in all of the patients, with one patient in particular requiring some treatment for the reaction.

Patients were then pre-treated with VISIPAQUE®320 (iodixanol). Exposure to cat allergen diluted 1:100 following the VISIPAQUE®320 pretreatment was not associated with any symptoms. Exposure to allergen diluted 1:10 following the VISIPAQUE®320 pretreatment was associated with mild reactions, similar to the exposure to the 1:100 dilution without the VISIPAQUE®320 pretreatment.

Patients were pre-treated with Iotrolan 280. Exposure to allergen diluted 1:10 following the Iotrolan 280 pretreatment was associated with mild reactions as well.

Table 1 summarizes the results and symptoms after exposure to a 1:10 dilution of cat allergen both with and without pretreatment with VISIPAQUE®320 or Iotrolan 280. The pretreatment resulted in a decreased reaction to the cat allergen compared to the reaction without pretreatment.

TABLE 1

| | No Pretreatment | Visipaque 320 Pretreatment | Iotrolan 280 Pretreatment |
|---|---|---|---|
| Itch | 11+ | 1+/− | 0 |
| Drip | 11+ | 1+/− | 1+ |
| Congestion | 11+ | 2+ | 1+ |
| Total | 33+ | 4+ | 2+ |
| Sneezes | 5× | 2× | 2× |

Example 12

A single-blind study was conducted using three human patients. Patients were pre-treated with VISIPAQUE®320 (Iodixanol) or not treated with contrast media. The patients were exposed to cat allergen at three different dilutions, 1:1000, 1:100, and 1:10. Patient symptoms of itch, drip, congestion, and sneeze were assessed.

Tables 2-4 show the results and symptoms after exposure to the indicated dilution of cat allergen both with and without pretreatment with VISIPAQUE®320. The pretreatment resulted in decreased symptoms in response to the cat allergen compared to the reaction without pretreatment.

TABLE 2

Patient 1

|  | No Pretreatment | Visipaque 320 Pretreatment |
|---|---|---|
| 1:1000 concentration cat allergen | | |
| Itch | 2+ | 0 |
| Drip | 1+ | 0 |
| Congestion | 0 | 0 |
| Sneezes | 0 | 0 |
| 1:100 concentration cat allergen | | |
| Itch | 1+ | 0 |
| Drip | 1+ | 0 |
| Congestion | 1+ | 0 |
| Sneezes | 0 | 0 |
| 1:10 concentration cat allergen | | |
| Itch | 1+ | 0 |
| Drip | 3+ | 1+ |
| Congestion | 3+ | 1+ |
| Sneezes | 1×+ | 2× |

TABLE 3

Patient 2

|  | No Pretreatment | Visipaque 320 Pretreatment |
|---|---|---|
| 1:1000 concentration cat allergen | | |
| Itch | 1+ (eye) | 0 |
| Drip | 1+ | 0 |
| Congestion | 0 | 0 |
| Sneezes | 0 | 0 |
| 1:100 concentration cat allergen | | |
| Itch | 2+ (eye) | 0 |
| Drip | 2+ | 0 |
| Congestion | 1+ | 0 |
| Sneezes | 1× | 0 |
| 1:10 concentration cat allergen | | |
| Itch | 2+ | 0 |
| Drip | 2-3+ | 0 |
| Congestion | 2-3+ | 0 |
| Sneezes | 1× | 0 |

TABLE 4

Patient 3

|  | No Pretreatment | Visipaque 320 Pretreatment |
|---|---|---|
| 1:1000 concentration cat allergen | | |
| Itch | 0 | 0 |
| Drip | 1+ | +/− |
| Congestion | 1+ | 0 |
| Sneezes | 0 | 0 |
| 1:100 concentration cat allergen | | |
| Itch | 1+ | 0 |
| Drip | +/− | 0 |
| Congestion | 0 | 0 |
| Sneezes | 1× | 0 |
| 1:10 concentration cat allergen | | |
| Itch | 1+ | +/− (ear) |
| Drip | 2+ | 0 |
| Congestion | 2+ | 1+ |
| Sneezes | 1× | 2× |

In a similar study, patients were treated with Iotrolan 280 prior to exposure to 1:10, 1:100, or 1:1000 dilutions of cat allergen. The effects of Iotrolan 280 treatment on the symptoms following exposure to cat allergen were similar to the effects seen with the VISIPAQUE®320 treatment., summarized in Tables 2-4.

Example 13

FIG. 1 is a photograph showing the response of the patient to 6 injections. Three substances were each injected twice at two different locations, for a total of 6 injections. Each substance was injected at one location that had been pretreated with CHOLOGRAFIN® meglumine and at a second location that had not been pretreated. CHOLOGRAFIN® meglumine, which comprises 80% Iodipamide in emollient, was applied topically to part of a patient's arm. Forty five minutes after application of the CHOLOGRAFIN® meglumine, each of the three substances was injected into the two different locations on the arm, one pretreated and one that was not pretreated.

The three substances were histamine, dust allergen, and grass allergen. Referring to FIG. 1, the two histamine injections went into the upper level of the arm, the two dust allergen injections went into the middle level of the arm, and the two grass allergen injections went into the lower level of the arm.

FIG. 1 is a photograph showing the resulting reactions taken 2.5 hours after the injections. The left side of FIG. 1 shows the reactions sites corresponding to the untreated side of the arm and the right side of FIG. 1 show the sites corresponding to the pretreated side of the arm.

The reactions of upper, middle and lower levels of the arm on the untreated sides were rated with scores of 3+, 4+, and 4+, respectively. The reactions of the upper, middle and lower levels of the arm on the pretreated sides were rated with scores of 1+, 2+, and 2+, respectively. The decreased reactions on the pretreated side of the arm demonstrate that iodipamide acts caused a decreased reaction to histamine, dust allergen and grass allergen.

What is claimed is:

1. A method of treating a common cold in a mammal, comprising administering a therapeutically effective amount of a composition comprising an X-ray contrast media to the mammal, wherein the X-ray contrast media comprises tri-iodinated, completely or partially substituted, benzene moieties existing in a form of a monomer or an ionic dimer.

2. The method of claim 1, wherein the treating the common cold comprises treating a symptom of the common cold.

3. The method of claim 2, wherein the symptom is a stuffy nose, nasal congestion, or a cough.

4. The method of claim 1, wherein the x-ray contrast media is selected from the group consisting of iopamidol, ioversol, iopromide, iohexol, iothalamate, diatrizoate, ioxaglate, iodipamide, iodixanol, iotrolan, tyropanoate and iopanoic acid.

5. The method of claim 1, wherein the X-ray contrast media is in the form of an ionic dimer.

6. The method of claim 1, wherein the X-ray contrast media comprises ioxaglate or iodipamide.

7. A method of treating nasal congestion in a mammal, comprising administering a therapeutically effective amount of a composition comprising an X-ray contrast media to the mammal, wherein the X-ray contrast media comprises tri-iodinated, completely or partially substituted, benzene moieties existing in a form of a monomer or an ionic dimer, and wherein the nasal congestion is a result of a common cold.

8. The method of claim 7, wherein the x-ray contrast media is selected from the group consisting of iopamidol, ioversol, iopromide, iohexol, iothalamate, diatrizoate, ioxaglate, iodipamide, iodixanol, iotrolan, tyropanoate and iopanoic acid.

9. The method of claim 7, wherein the X-ray contrast media is in the form of an ionic dimer.

10. The method of claim 7, wherein the X-ray contrast media comprises ioxaglate or iodipamide.

11. The method of claim 1 or 7, wherein the composition further comprises a preservative.

12. The method of claim 1 or 7, wherein the mammal is a human.

13. The method of claim 1 or 7, wherein the administering comprises contacting at least part of an affected area of the mammal with the composition.

14. A method of treating a common cold in a mammal, comprising administering a therapeutically effective amount of a composition comprising an X-ray contrast media to the mammal, wherein the X-ray contrast media comprises tri-iodinated, completely or partially substituted, benzene moieties existing in a form of an ionic dimer, and wherein the administering comprises contacting at least part of an affected area of the mammal with the composition.

15. A method of treating nasal congestion in a mammal, comprising administering a therapeutically effective amount of a composition comprising an X-ray contrast media to the mammal, wherein the X-ray contrast media comprises tri-iodinated, completely or partially substituted, benzene moieties existing in a form of an ionic dimer, wherein the administering comprises contacting at least part of an affected area of the mammal with the composition, and wherein the nasal congestion is a result of a common cold.

* * * * *